US007415864B1

(12) United States Patent  (10) Patent No.: US 7,415,864 B1
Israel et al.  (45) Date of Patent: Aug. 26, 2008

(54) ORIFICE TEST DEVICE FOR PROTECTIVE MASK TESTERS

(75) Inventors: Joshua D. Israel, Baltimore, MD (US); Corey L. Piepenburg, Nottingham, MD (US); Malcolm D. Goodman, Forest Hill, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 260 days.

(21) Appl. No.: 11/468,943

(22) Filed: Aug. 31, 2006

(51) Int. Cl.
 *G01N 15/02* (2006.01)
 *A62B 7/10* (2006.01)
(52) U.S. Cl. .................... 73/1.02; 73/1.24; 73/1.56
(58) Field of Classification Search ............. 73/1.02, 73/1.24, 1.56, 865.5; 356/335, 336, 337–343; 128/201.22–201.25, 205.27–205.29, 206.21, 128/206.28
 See application file for complete search history.

(56) References Cited

U.S. PATENT DOCUMENTS

| 2,442,187 | A | * | 5/1948 | Tremain | 73/38 |
| 4,146,025 | A | * | 3/1979 | Warncke et al. | 128/201.23 |
| 4,846,166 | A | * | 7/1989 | Willeke | 128/200.24 |
| 5,059,350 | A | * | 10/1991 | Carlon et al. | 252/408.1 |
| 5,059,351 | A | * | 10/1991 | Carlon et al. | 252/408.1 |
| 5,059,353 | A | * | 10/1991 | Carlon et al. | 252/408.1 |
| 5,076,965 | A | * | 12/1991 | Guelta et al. | 252/408.1 |
| 5,094,779 | A | * | 3/1992 | Carlon et al. | 252/408.1 |
| 5,289,819 | A | * | 3/1994 | Kroger et al. | 128/200.24 |
| 5,320,108 | A | * | 6/1994 | Cloutier | 600/529 |
| 5,747,667 | A | * | 5/1998 | Sadar | 73/1.02 |
| 7,343,782 | B2 | * | 3/2008 | Damer et al. | 73/31.03 |
| 2003/0029221 | A1 | * | 2/2003 | Juneau et al. | 73/1.02 |

FOREIGN PATENT DOCUMENTS

| DE | 2550594 A1 * | 5/1977 |
| GB | 2430255 A * | 3/2007 |
| SU | 715089 A * | 2/1980 |
| WO | WO 8702898 A1 * | 5/1987 |

* cited by examiner

*Primary Examiner*—David A. Rogers
(74) *Attorney, Agent, or Firm*—Ulysses John Biffoni

(57) ABSTRACT

An orifice test calibration device tests the functionality of protective mask testers. The orifice test calibration device has a semi-rigid tubular channel with one end for sealing the flow outlet port of the protective mask tester and a second end for sealing the vacuum inlet port of the protective mask tester. The device also includes a sealable opening within the tubular channel and an insertable orifice plug having a set diameter for insertion into the sealable opening in order to calibrate the protective mask tester.

8 Claims, 2 Drawing Sheets

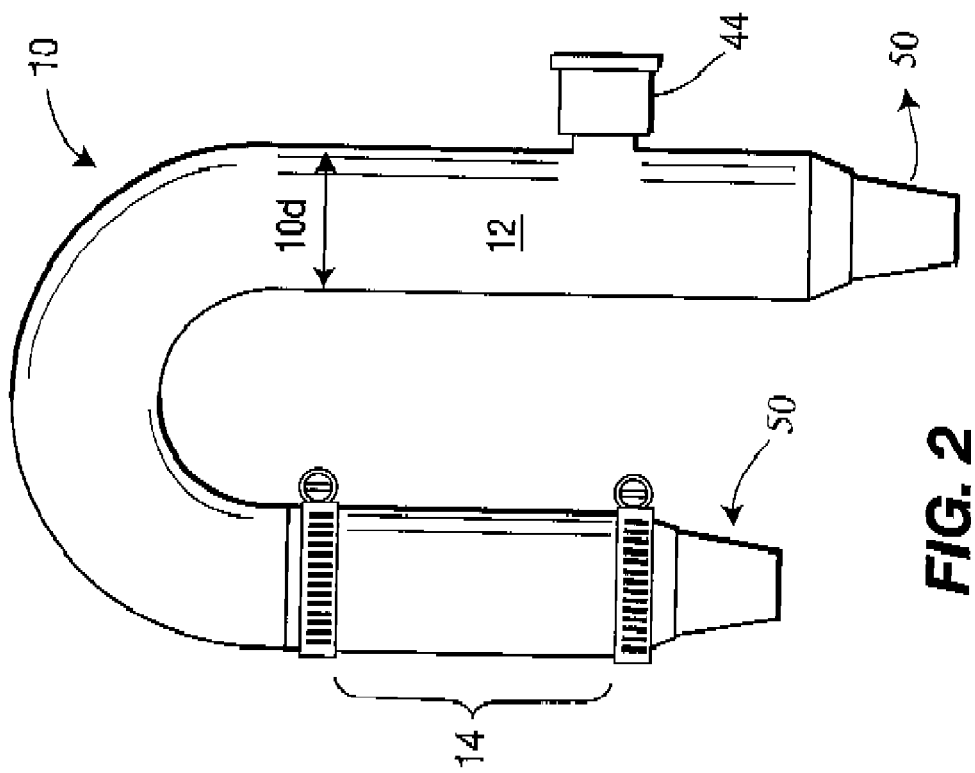
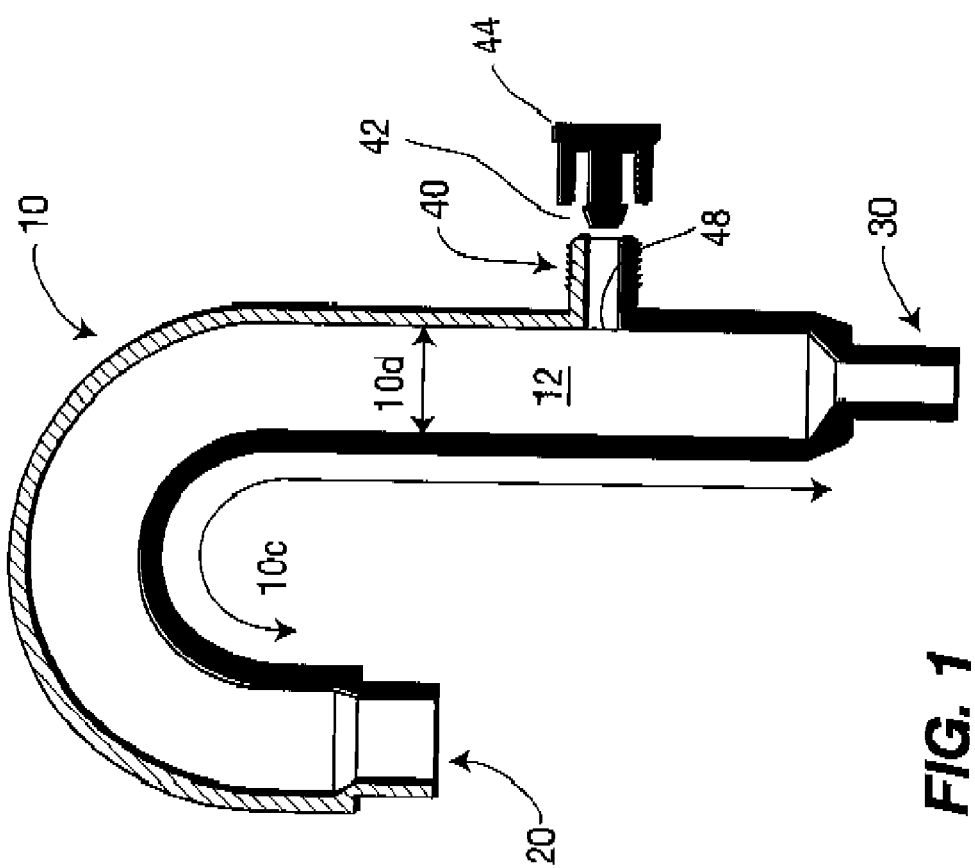
FIG. 1
FIG. 2

ORIFICE TEST DEVICE FOR PROTECTIVE MASK TESTERS

GOVERNMENT INTEREST

The invention described herein may be manufactured, licensed, and used by or for the U.S. Government.

BACKGROUND OF THE INVENTION

1. Field of the Invention

This present invention relates to orifice test calibration devices for testing the functionality of a protective mask tester.

2. Brief Description of the Related Art

Protective respiratory masks protect the wearer's face, eyes, and lungs from the effects of hazardous airborne chemical or biological agents under circumstances such as soldiers operating in a chemically or biologically contaminated environment. Protective masks may additionally be used in numerous other operating environments, such as firefighting, environmental cleanup, manufacturing, medical hazard handling, quarantining of patients with highly contagious pathogens, biological and chemical warfare, mining, paint applications, construction, and other applications where persons may come into contact with hazardous substances especially airborne hazards. Typically, the protective mask is worn over the wearer's face and seals the face from the ambient atmosphere. The protective mask cleans the air entering the mask by means of a filter device generally having chemically impregnated fibers, HEPA filters, and a bed of adsorbent material such as activated charcoal. During operation, a one-way inlet valve in the mask allows air drawn in by the wearer's lungs to pass through a filter containing the filtration media to provide a flow of filtered air into the mask. As the wearer exhales, the exhaled gas is expelled through a one-way outlet valve out of the mask and the process is repeated with each breath.

The protective mask provides the wearer with protection from toxic airborne substances only with proper fit and function. Therefore, it is extremely important that the mask be properly tested to ensure that it will protect the wearer from these life threatening agents. Proper testing of the protective masks requires that the protective mask testers be properly calibrated. Gas mask testers, such as the Army's M14, commercially available TDA-99M, TDA-99B, TDA-104, Q204 and the Joint Service Mask Leakage Tester (JSMLT), provide a platform for testing the serviceability of gas masks particularly with regard to leakage of the mask. These testers may be portable or fixed devices having clamping mechanisms, inflatable mask seals and clamping adapters for fixing the masks in place for testing. For example, the assessment process of a protective mask using the portable TDA-99M Respirator Function Tester uses a microprocessor to test the reliability of the functional components of the mask, testing for overall mask integrity, the drink train functions and outlet valve assembly operation. The TDA-99M is a self-contained unit with an inflatable mask seal, different sized headforms and several adapters that permit leak testing of protective masks. The assessment process begins with a visual inspection of each mask for numerous specified defects followed by a mechanical evaluation using the TDA-99M. During the mechanical testing process, the mask is strapped on the tester's headform and covered with a shroud. The mask seal is then inflated, sealing the mask to mimic a proper fit. Inflatable seals generally include a conventional solenoid fill port through which pressurized air is directed to inflate the seal. Once the seal is inflated, a fine, non-toxic aerosol is dispersed inside the shroud and on the outside of the protective mask. The TDA-99M creates a pressure differential between the interior and exterior of the protective mask, i.e., it attempts to draw the aerosol through the protective mask, using a vacuum within the protective mask area while simultaneously sampling the air inside the protective mask. If the air inside the protective mask is unacceptable, an alarm sounds to indicate the protective mask is leaking. The protective mask, once passing the overall leakage test, is tested for problems associated with the drink train and outlet valve assembly. However, the protective mask testers only provide adequate validation of the protective masks when the protective mask testers are properly calibrated. Generally, these systems do not have external testing devices to verify the tester devices are working properly.

There is a need in the art for mechanisms to provide reliable and efficient calibration of protective mask testers. The present invention addresses these and other needs.

SUMMARY OF THE INVENTION

The present invention includes an orifice test calibration device for testing the functionality of a gas mask tester, said calibration device having a semi-rigid tubular channel with a first end effective for sealing a first head piece flow outlet of a protective mask tester and a second end effective for sealing a second head piece vacuum inlet of a protective mask tester, a sealable opening within the tubular channel and an insertable orifice plug for insertion into the sealable opening, wherein the orifice plug has a set opening diameter. The orifice test calibration device is inserted into the flow and vacuum ports on the head piece of the gas mask tester. With the presence of the detectable airborne particles in the exterior environment of the orifice test calibration device, a vacuum is concurrently drawn within the orifice test calibration device and the air flow is monitored for the presence of the airborne particles.

BRIEF DESCRIPTION OF THE DRAWINGS

FIG. 1 illustrates a cut-away, side view of the orifice test calibration device of the present invention;

FIG. 2 illustrates a side view of the orifice test calibration device of the present invention having a bending portion therein; and, FIG. 3 illustrates the orifice test calibration device of the present invention in use on the test head of a protective mask tester.

DETAILED DESCRIPTION OF THE PREFERRED EMBODIMENT

Figure 3:
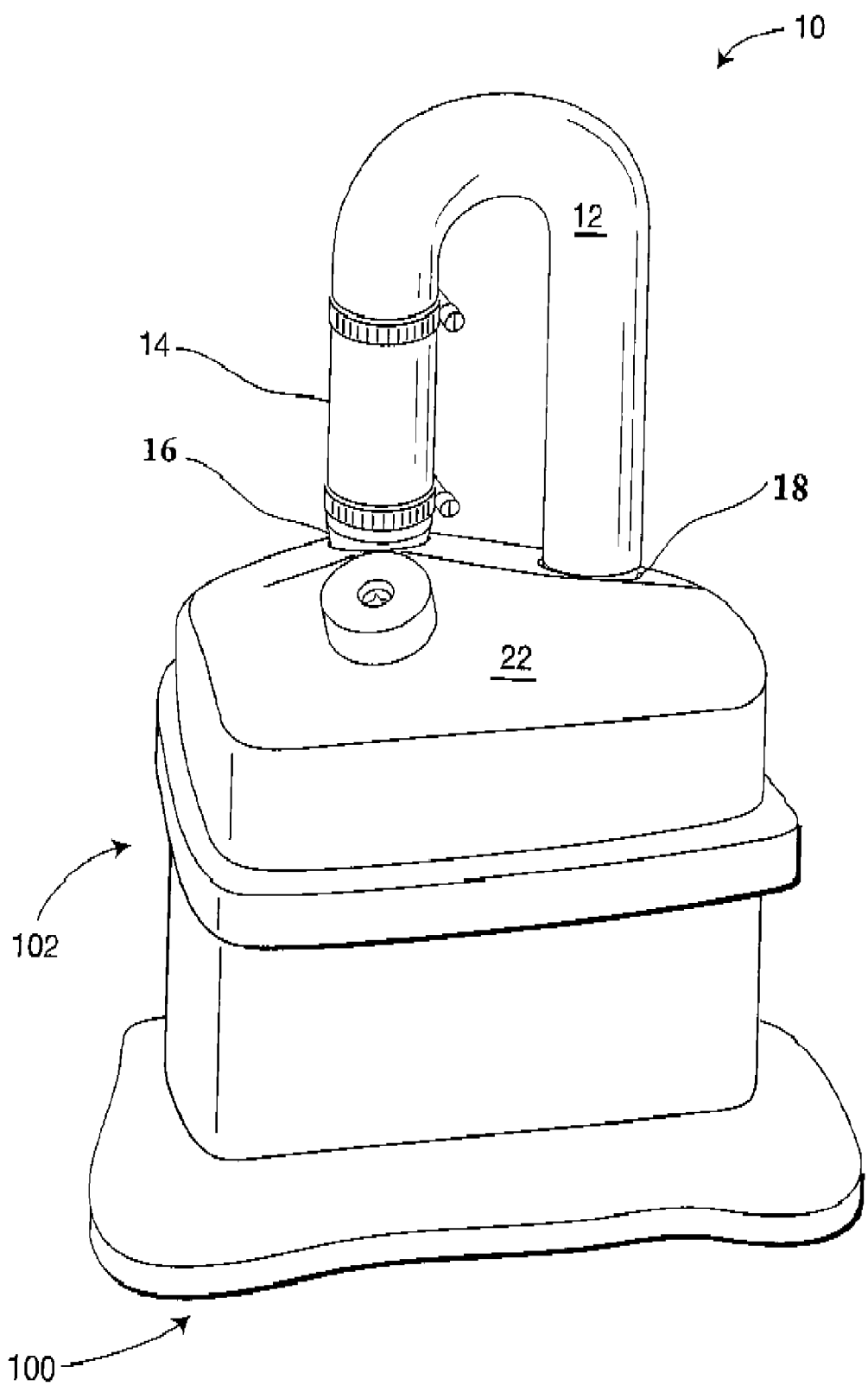

The orifice test calibration device of the present invention is used for testing the functionality of protective mask testers, which are used to test protective masks. The present invention functionally re-routes air from the outlet of a head piece of the mask tester to the inlet of the head piece of the mask tester, providing a measurement of airflow by means of an orifice device while maintaining a vacuum within the system.

As seen in FIGS. 1, 2 and 3, the present invention includes an orifice test calibration device 10 used to test protective mask testers 100. The protective mask testers 100 generally include a head piece, also referred to as a test head or headform, 102. The head piece 102 is generally configured to hold a protective mask in place during testing. Typically, the head piece 102 has a polyurethane composition; however, it will be readily appreciated that the material of the head piece 102 can be readily varied. While head piece 102 typically accommodates a full, face-seal type protective mask, other head piece 102 configurations may be readily used to accommodate half, face-seal type or full, neck-seal type protective masks. Representative protective mask testers 100 useful for calibration with the present invention include, for example, protective mask testers such as the M14, TDA-99M, TDA-99B, TDA-104, Q179, Q204, JSMLT mask leakage testers, and other like testing equipment used to ensure the reliability and non-leakage of protective masks, such as gas masks. For example, the TDA-99M Protective Mask Leakage Tester, NSN 6665-01-450-3022, is manufactured by ATI, Inc., and is a portable unit having a universal power supply and internal compressed air source. This device provides leak testing of specific components without requiring a user to wear the mask, such as testing of overall mask leakage, leakage isolation, outlet valve, drink tube flow, drink tube valve leakage, drink train leak, and quantitative fit. Operation instructions for the mask testers are provided by the manufacturer in common instruction manuals, such as the ATI Data Acquisition System 1 (DAS 1) Operator's Manual 1800109A, published by Air Techniques International (ATI), a division of Hamilton Associates, Inc., of Owings Mills, Md., the disclosure of which is herein incorporated by reference. Representative protective masks that are tested on these protective mask testers 100 include chemical and/or biological masks that are required to completely partition the air residing on the interior and exterior sides of the protective mask such that only filtered air may enter the mask. Such protective masks may include, for example, the U.S. Army's M17 protective mask, the M40 series protective mask, the M42 series protective mask, the M45 protective mask, MCU2/P mask, the Joint Service General Purpose Mask (JSGPM), and the like. These protective masks are generally found in use by the United States military.

Referring to FIGS. 1 through 3, the orifice test calibration device 10 has a U-shaped configuration made of a semi-rigid material with a shorter end 20 and a longer end 30. The U-shaped configuration forms a semi-rigid tubular channel 12. The shorter end 20 of the semi-rigid tubular channel 12 provides a sealable end for insertion into a flow outlet port 16 located on the head form 102 of the protective mask tester 100. Similarly, the longer end 30 provides a sealable end for insertion into a vacuum port 18 located on the head form 102 of the protective mask tester 100. The two ends 20 and 30 are designed to effectively seal both the flow outlet port 16 and vacuum inlet port 18 on the top surface 22 of the head piece 102 on the protective mask tester 100. The orifice test calibration device 10 is sized to extend between the two ports 16 and 18, flow and vacuum, with give within the semi-rigid tubular channel 12 that allows it to flex across a lateral range of motion for a sealable fit within the ports of the protective mask tester 100, such as from about 1 inch to about 3 inches. As seen in FIG. 2, the orifice test calibration device 10 may further include a bendable section 14 of the semi-rigid tubular channel 12 that significantly increases the lateral flexibility of the orifice test calibration device 10. The bendable section 14 also may be used to ensure conformity of the length of the channel 12 with the distance between the flow and vacuum ports. Referring to FIG. 2, the bendable section 14 may be an integral part of the semi-rigid tubular channel 12, or may be incorporated onto the channel 12 as a component part thereof. When the bendable section 14 is added as a separate component piece, sealing bands, such as Oetiker hose clamps, may be attached to the tubular channel 12 and rubber stopper inserts 50 (described below) to ensure an air-tight fit onto the channel 12 and to become a component thereof. The orifice test calibration device 10 includes a sufficient length 10c to conveniently extend the distance between flow port 16 and vacuum port 18 of a given head piece 102 and a cross-sectional diameter 10d to effectively manipulate the orifice test calibration device 10 during insertion and removal from the head form 102. This allows a single orifice test calibration device 10 of the present invention to be useful in various head pieces 102 for different sizes, e.g., small, medium and large, and different makes of testers. Representative lengths 10c of the orifice test calibration device 10 include for example, without limitation, from about 5 inches to about 12 inches, with more preferred lengths including from about 6 inches to about 8 inches. Additionally, representative diameters 10d of the orifice test calibration device 10 include from about 0.5 inch to about 1.5 inch, such as 0.75 inch, with wall thickness appropriate for maintaining vacuum within the orifice test calibration device, such as from about 0.02 inches to about 0.04 inches, generally depending on the material used.

In one embodiment, the orifice test calibration device 10 has a clear/transparent resilient composition that slightly bends along its length 10c. Representative compositions of the orifice test calibration device 10 include, for example, plastic and other plastic-like polymer compositions such as Tygon tubing. Manufacture of the orifice test calibration device 10 may include any appropriate manufacturing process for construction of a orifice test calibration device 10 capable of achieving an air-tight seal between the flow and vacuum ports of the head piece 102 on a protective mask tester 100. Representative manufacturing methodologies for the present invention include compression or injection molding processes, with such processes well-known in the art for creation of transparent unitary forms of plastic compositions.

Rubber stopper inserts 50 are preferably located at the first end 20 and second end 30 to ensure a reliable air-tight fit of the orifice test calibration device 10 with the fixed holes within the head piece 102 that constitute the flow port 16 and vacuum port 18 of the protective mask tester 100. These rubber stopper inserts 50 may be attached by any appropriate means to secure the rubber stopper inserts 50 onto the first end 20 and second end 30 of the orifice test calibration device 10, such as with the application of an epoxy or other similar adhesive material. The rubber stopper inserts 50 are positioned around areas of reduced diameter of the first end 20 and second end 30 of the orifice test calibration device 10 for effectively fitting, typically by insertion, into the flow and vacuum ports of a given test head 102. The semi-rigid tubular channel 12 of the orifice test calibration device 10 preferably includes a longitudinally rigid composition, i.e., along the length of the channel 12, that provides additional rigidity for pressing the first end 20 and second end 30 into the flow port 16 and vacuum port 18 of the protective mask tester 100.

Within the length of the orifice test calibration device 10, a sealable opening 40 is formed within the tubular channel 12. This sealable opening 40 provides a seat for locating an insertable orifice plug 42 therein, creating a barrier to stop simulant from inadvertently passing therethrough. The sealable opening 40 includes a set opening diameter that accommodates insertion of a given orifice plug 42 designed for a specific sized screening surface. The sealable opening 40 may include any appropriate size or shape for application of an appropriately sized orifice plug 42 thereto, with preferred sizes ranging from about 0.25 inches or greater in circumference with more preferred circumferences ranging from about 0.25 inch to about 0.5 inch. The specified screening surface includes particle restriction sizes for restricting simulant, e.g., aerosol, etc., therethrough, with restriction diameters within the sealable opening 40 ranging across any appropriate size for air particle testing, such as from less than about 20 microns to greater than 120 microns, with preferred restriction diameters ranging from about 20 microns to about 120 microns, and more preferably from about 30 microns to about 40 microns. Manufacture of the restriction diameters of the insertable orifice plug 42 may be accomplished by any appropriate process for correct sizing of the inlet, such as by laser drilling.

Preferably, the sealable opening 40 includes a cap or capping device 44 that is used to retain and secure the insertable orifice plug 42. The cap device 44 has an opening that permits the free flow of air to the inserted orifice plug 42 therein. A blank orifice plug 42, i.e., an orifice plug having no orifice therein, may be inserted into the sealable opening 40 and secured by the cap 44 during non-use of the orifice test calibration device 10. Most preferably, the cap 44 is threaded onto the sealable opening 40 to provide a reliable air-tight seal between the cap 44 and sealable opening 40 while allowing air flow through the insertable orifice plug 42. Additional features of the sealable opening 40 may include a face sealing o-ring component 48 within the sealable opening 40, and/or latching devices and the like for further securing an airtight seal of the sealable opening 40. In one embodiment, the o-ring 48 is permanently fixed within the orifice test calibration device 10. When present, the o-ring 48 preferably seals the insertable orifice plug 42 against the tubular channel 12 in an air-tight manner.

In use, the orifice test calibration device 10 of the present invention tests the functionality of a protective mask tester 100. The orifice test calibration device 10 retains an orifice plug 42 that rests firmly against the o-ring 48 and cap 44 to create a controlled leakage chamber. The orifice test calibration device 10 is fixed to a protective mask testing head piece 102, with the orifice test calibration device 10 providing a conduit between the flow port 16 and vacuum port 18 of the head piece 102, sealing the conduit from outside air, i.e., the orifice test calibration device 10 provides an air-tight juncture between the ports. The rubber stopper inserts 50 located at the first end 20 and second end 30 of the orifice test calibration device 10 are inserted into the flow port 16 and vacuum port 18, respectively, of the head piece 102 of the protective mask tester 100. A covering for containing a detectable airborne composition is typically placed over the mask tester 100 and the orifice test calibration device 10 to contain a detectable airborne composition within a containment area, with such covering being a plastic or other like impermeable material. As such, an operator generally restricts the environment adjacent to the head piece 102 by placing a conventional containment shroud over the head piece 102. Once the shroud is in place, the operator inserts an aerosol hose through an opening in the containment shroud. Preferred detectable airborne compositions include aerosols, with the detectable airborne composition outside of the orifice test calibration device 10 preferably maintained at about atmospheric pressure. Most preferably, the test aerosol agent (detectable airborne composition) is polyalphaolefin (PAO) which has been approved for use by the U.S. Army Surgeon General, the Department of the Energy and the Federal Food and Drug Administration. However, it will be readily appreciated that if detection other than photometry is used, e.g., condensate nuclei counting (CNC), the test agent may be varied. An aerosol generator is used by the operator to input a given aerosol into the shroud, generally adjusted to a minimum concentration within the shroud. Once the orifice test calibration device 10 is inserted into the mask tester 100 and the shroud is in place with the aerosol concentration adjusted to a desired value, a vacuum is drawn within and through the orifice test calibration device 10. Preferably the air-flow within the tubular channel 12 is filtered air that is maintained at a pressure of from about 5.5 inches $H_2O$ to about 6.5 inches $H_2O$, with other pressures possible as appropriate. The air flow within the orifice test calibration device 10 is then monitored for the presence of any of the detectable airborne composition. When the aerosol residing in the shroud flows into the vacuum port containing a scattering chamber, the aerosol particles scatter light emitted from a light source resulting in light striking a photomultiplier tube. This provides an indication of contamination entering the orifice test device 10. Using the blank orifice plug (no opening) 42, substantially no aerosol should be detected, e.g., leakage readings of from about 0.0000 to about 0.0002. Then, the blank orifice plug 42 is replaced by a laser drilled orifice plug 42 having a specified internal restriction diameter. Once the orifice is in place, another test is conducted. Based on previously determined data, a set range for the simulant is expected to flow through the orifice. When the leakage rate falls within the set range, the tester is functioning properly. When the leakage rate falls outside of the set range, the tester is retested. When the tester continually registers test results outside of the set range, the tester may be found to not be accurately counting the simulant passing through the orifice test calibration device 10. The protective mask testers 100 that are adequately tested using the orifice test calibration device 10, and shown to be functional, provide reliable platforms for continued testing of protective masks.

EXAMPLE 1

A TDA-99M Protective Mask Tester is tested for proper functionality. An orifice test calibration device 10 of the present invention is inserted in the flow port 16 and vacuum port 18 of the head piece 102 and a shroud is placed over the inserted orifice test calibration device 10 and the head piece 102. The orifice test calibration device 10 has an inserted orifice plug 42 having a blank orifice (no opening). An aerosol is flowed into the shroud, outside of the orifice test calibration device 10. The tubular channel is subjected to a vacuum of about 6.0 inches $H_2O$. Substantially no aerosol is detected by the TDA-99M Protective Mask Tester 100, with leakage readings of from about 0.0000 to about 0.0002 showing that the orifice test calibration device 10 is functioning. The blank orifice plug 42 is replaced by a laser drilled orifice plug 42 having an internal restriction diameter of 120 microns. Once the orifice plug 42 is in place, a second test is conducted. Based on previously determined data, a set range for the simulant is expected to flow through the orifice. When the leakage rate falls within the set range, the tester is functioning properly. When the leakage rate falls outside of the set range, the tester is retested. When the tester continually registers test results outside of the set range, the tester is found to not be accurately counting the simulant passing through the orifice test calibration device 10 and not properly calibrated.

The foregoing summary, description, and examples of the present invention are not intended to be limiting, but are only exemplary of the inventive features which are defined in the claims. Alternative materials and configurations as those described herein for the present invention may be used.

What is claimed is:

1. A method for testing the functionality of a protective mask tester, comprising the steps of:
   providing an orifice test calibration device comprising: a semi-rigid tubular channel having a first end effective for sealing a mask head piece flow port and a second end effective for sealing a mask head piece vacuum port of said protective mask tester; a sealable opening within the tubular channel; and, an insertable orifice plug for insertion into the sealable opening, wherein the orifice plug has a set opening diameter;

inserting the orifice test calibration device into the flow port and the vacuum port of the protective mask tester;

flowing a detectable airborne composition outside of the orifice test calibration device; and, drawing a vacuum within the orifice test calibration device, wherein the air flow within the orifice test calibration device is monitored for the presence of the detectable airborne composition.

2. The method of claim 1, further comprising covering and containing the detectable airborne composition over the orifice test calibration device.

3. The method of claim 1, wherein the detectable airborne composition comprises an aerosol.

4. The method of claim 1, wherein the detectable airborne composition outside of the orifice test calibration device is maintained at about atmospheric pressure.

5. The method of claim 1, wherein the air-flow within the tubular channel comprises filtered air.

6. The method of claim 1, wherein the air pressure inside of the tubular channel ranges from about 5.5 inches $H_2O$ to about 6.5 inches $H_2O$.

7. The method of claim 1, wherein the orifice plug has an opening of from about 20 microns to about 150 microns.

8. The method of claim 7, wherein the orifice plug has an opening of about 30 microns to about 40 microns.

* * * * *